May 20, 1947. D. E. MORRISON ET AL Re. 22,880
BONDED JOINT OR SECTION OF ELASTIC FABRIC
Original Filed June 12, 1940
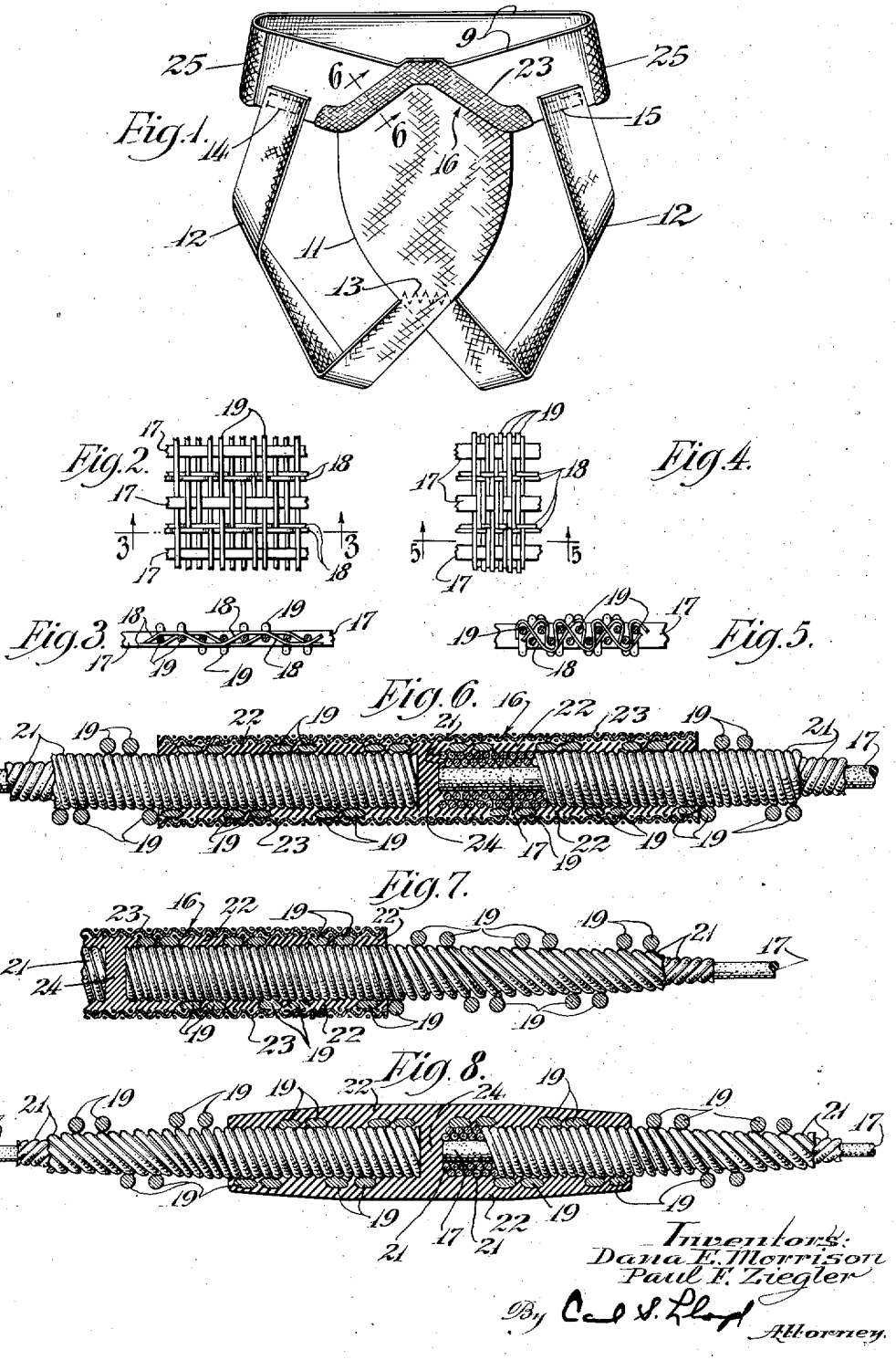
Inventors:
Dana E. Morrison
Paul F. Ziegler
By Carl S. Floyd
Attorney.

Reissued May 20, 1947

Re. 22,880

UNITED STATES PATENT OFFICE 22,880

BONDED JOINT OR SECTION OF ELASTIC FABRIC

Dana E. Morrison, Kenilworth, and Paul F. Ziegler, Winnetka, Ill., assignors to The Kendall Company, Chicago, Ill., a corporation of Massachusetts Original No. 2,380,365, dated July 10, 1945, Serial No. 340,008, June 12, 1940. Application for reissue June 21, 1946, Serial No. 678,206

19 Claims. (Cl. 128—159)

This invention has for its principal object the improvement of joints between sections of garments in which one or more of the sections to be joined is made of elastic fabric.

Such joints in athletic supporters and other elastic articles have presented a difficult problem in the past due largely to the changes in condition of the elastic fabric between its relaxed state and its stretched state. The repeated stretching and relaxing of the fabric has caused the joint to give way before the garment was otherwise worn out and has otherwise impaired the utility and durability of the garment, as will be better understood by considering the following description of structure of such fabric and the changes in condition which occur in normal usage.

The usual type of elastic fabric comprises textile threads woven or knitted together, with rubber threads extending therethrough, the rubber threads being ordinarily covered by other textile threads wrapped or braided around the same, although these covering threads may be omitted if desired. The exact structure of the fabric and the method of fabricating it may of course vary according to the uses to which the fabric is to be put and the particular characteristics desired.

In the relaxed state the textile threads or yarns and also the rubber threads are under comparatively low tension; the fabric is thick as compared with the stretched state and the degree of crimp in the threads, especially the textile threads, is high; the rubber threads are large in cross section; the interstices between the interlaced threads are small; and relatively small portions of the surfaces of the various threads are at the surface of the fabric.

In the stretched state substantially the reverse of the above conditions prevail, and in changing from one condition to another there is relative movement between the threads, with no fixed relation maintained between the above-described elements of the fabric. There is a tendency for the rubber threads to retreat or move through the fabric and the ends of such threads, unless effectively restrained, are likely to be in a different position after stretching of the fabric than they were before. This may result from pulling out of threads from the joint, which is especially likely to occur if the joint is at an angle or on a curve, or from breaking of the threads or severance of them by the needles of a sewing machine if the joint is formed by sewing.

In the past, joints containing elastic fabric have usually been made by sewing or stitching (sometimes with the edge of the fabric doubled back so as to make the pulling out of the threads more difficult) or by the use of metal clamps of one form or another. In the case of sewed joints it has been the practice in some instances to impregnate the area around the joint with rubber solutions or rubber latex with a view to preventing the receding of broken or severed rubber threads. Sometimes the fabric has been treated before sewing and sometimes afterward, but in every instance of which we are aware the strength of the joint has depended upon the sewing. The interstices of the fabric have been only partially filled and the treated area has remained to a considerable extent elastic and subject to the changing internal conditions resulting from stretching and relaxing. The impregnation has merely tied the rubber threads more or less firmly to the textile threads and while this has tended to delay the receding of rubber threads due to the causes above-mentioned, thus delaying the failure of the joint, it has not prevented the internal changes which ultimately bring the failure.

Our invention provides a joint made without sewing or the use of metal clamps which effectively prevents the changes in condition of the fabric due to stretching and relaxing which have been the principal cause of the difficulties previously experienced.

While we have thus far referred only to joints, the invention from certain aspects is applicable to portions of an elastic fabric which it is desired to render immobile, i. e., not subject to stretch, whether the same enter into the joint or not. In other words, there may be reasons other than the strengthening of a joint for immobilizing a section of an elastic fabric, one example being shown in the accompanying drawing, and the invention is to be regarded as applying to such a section as well as to a joint. It is also applicable to the formation of a stay to maintain the shape and to prevent the curling of a garment such, for example, as a corset.

Other features of the invention and additional objects and advantages will be evident from the following description and the accompanying drawing, in which:

Fig. 1 is an elevational view of an athletic supporter in which the joint between the belt and pouch, and also certain sections of the belt, are constructed in accordance with my invention;

Fig. 2 is a plan view of a portion of the elastic fabric contained in the supporter, the same being shown in stretched condition;

Fig. 3 is a sectional view taken on the section line 3—3 of Fig. 2;

Fig. 4 is a view similar to Fig. 2 but showing the fabric in the relaxed state;

Fig. 5 is a sectional view taken substantially on the section line 5—5 of Fig. 4;

Fig. 6 is a magnified and somewhat schematic view in cross section of a joint made in accordance with my invention, the same being shown in the relaxed state of the fabric, and being taken substantially on the section line 6—6 in Fig. 1;

Fig. 7 is a similar view of a portion of the joint, the same being shown in the stretched state of the fabric; and Fig. 8 is a view similar to that of Fig. 6 but showing the parts in the stretched state of the fabric and omitting the facing strips on the surfaces of the bonding material which are shown in Figs. 6 and 7.

The supporter shown in Fig. 1 of the drawing, as an illustration of one embodiment of the invention, comprises a belt 9, to the front portion of which is attached a pouch 11, the lower end of which is connected to front side portions of the belt by means of leg bands 12, the latter being sewed or otherwise suitably secured to said lower end of the pouch, as indicated at 13, and to the belt at the points indicated by the numerals 14 and 15, respectively.

The joint between the upper part of the pouch and the belt is indicated generally in Fig. 1 by the reference numeral 16 and as shown, is of inverted V-shape, with the lines of juncture extending diagonally across the belt to substantially a point of convergence at the top. It will be understood that the invention is not restricted to this particular configuration or shape of joint, although it has special utility in connection with joints formed at angles or on curves since it overcomes difficulties especially experienced in connection with such joints, as has been previously pointed out.

The construction of the joint is shown in detail in Figs. 6 to 8, inclusive, but before referring more particularly to these figures it is desired to call attention to structural characteristics of the elastic fabric, as illustrated in Figs. 2 to 5, inclusive, it being understood that the pouch 11 and the belt 9 in the present instance are both made of elastic fabric. While the fabric of the pouch and that in the belt are different in specific form, both types of fabric contain rubber threads and the general characteristics are sufficiently indicated for present purposes in the above mentioned figures of the drawing. It will of course be understood that in some instances the joint may be used to connect a piece of elastic fabric to a piece of non-elastic fabric and the elastic fabric referred to herein may therefore be regarded as one or more of the materials entering into the joint.

In said Figs. 2 to 5 of the drawing, the rubber threads are indicated by the numeral 17, the textile threads extending in direction parallel to said rubber threads by the numeral 18, and the textile threads extending in direction at right angles to the above-mentioned threads by the numeral 19. Said threads are interlaced to form in the present instance what is sometimes referred to as a "basket weave," and it will be observed that there is a very decided change in condition of the fabric between the stretched state as shown in Figs. 2 and 3, and the relaxed state as shown in Figs. 4 and 5, the threads having a much higher degree of crimp in the latter state and the interstices in the fabric being much smaller, the same not even being shown in Fig. 4 since they would not be apparent with the fabric in the condition shown in this figure. The rubber threads are of course much smaller in diameter when the fabric is stretched and the possibilities of movement of these threads through the fabric will be apparent, particularly from Figs. 2 and 4. Furthermore, the change in relationship of the textile threads to each other as well as to the rubber threads, as between the stretched and relaxed states of the fabric, is clearly illustrated in these figures and in Figs. 3 and 5. The covering of textile threads on the individual rubber threads is not shown in Figs. 2 to 5, but is shown in Figs. 6 to 8, wherein said threads, which are wrapped spirally around the rubber threads, are indicated by the numeral 21.

The joint 16 comprises a bonding material 22 shown in Figs. 6 to 8 of the drawing and preferably also fabric facing strips 23 on one or both sides of the joint, such strips being shown in Figs. 6 and 7 but not in Fig. 8. The bonding material may be chosen from thermoplastic materials which are solid at ordinary temperatures and retain their thermoplastic properties after the temperature and pressure treatment used to form the joint, but is preferably chosen from materials which lose their plasticity after such treatment, such materials being commonly described as thermosetting materials. Examples of the former type of materials are unvulcanized rubber, cellulose esters and ethers, vinyl and acrylic resins; examples of the latter are vulcanizable rubber, phenol formaldehyde plastics and urea formaldehyde plastics. The proper degree of flexibility of the bonding material to meet the particular requirements of a joint can be obtained through plasticizer formulation. Said bonding material fills practically all of the interstices of the fabric in the area to which it is applied and adheres to practically all of the threads in the fabric. When the joint is a butt joint, i. e., one in which the fabric pieces do not overlap but are arranged edge to edge, said material fills the space between said edges, as indicated at 24 in the drawing, forming a link between the two pieces of fabric. In this regard it is also advantageous to select a bonding material which will firmly adhere to the end portions of the rubber strands, to further prevent them from being pulled out of the joint by repeated tension, although ordinarily the degree of compression on the textile threads along the length of rubber threads within the joint easily fulfills this requirement.

The bonding material may be applied by placing a strip thereof over the area to be bonded and applying heat and pressure thereto, preferably in a confined space, the material becoming plastic at a temperature lower than the scorch point of the fabric and being caused to flow into the interstices of the fabric so as to completely or substantially fill the same and to form a solid and substantially inelastic section or matrix including the contiguous portions of the pieces of fabric which are joined thereby. Milled rubber may be employed for this purpose and when heat and pressure are applied thereto, with the same confined in a closed mould, the fabric will be thoroughly and uniformly penetrated in a definitely confined area and a solid link will be formed between the edges of the fabric at the point indicated by the numeral 24. This will result in preventing changes in the internal condition of the fabric in the area of the joint, and will form a secure and durable joint without the use of stitching, metal clamps, or any means other than the bonding material itself.

Furthermore, it is possible to obtain an immobilized section of elastic fabric in desired form or shape by using a suitably shaped mould to form the bonding material during the above described process of heating under pressure. Said section, although the threads or strands therein are immobilized, may be sufficiently flexible to meet the requirements of the garment.

When the fabric facing strips 23 are employed, they may be applied prior to the application of heat and pressure, and the bonding material will be caused to flow through the interstices thereof, firmly joining the same to said material throughout the area thereof. Such strips are preferably made of non-elastic fabric and serve to further immobilize the bonded area as well as to provide a smooth surface, which is desirable in garments such as the one shown in Fig. 1 of the drawing. Furthermore, the use of such reinforcing strips allows a more varied selection of bonding materials than would otherwise be feasible, since not only can materials with surfaces which would otherwise be too rough for garments of this character be used, but materials with more elasticity and plasticity and less tensile strength and tear resistance can be employed without impairing the strength of the joint, as the reinforcing strips can take over part of the load on the joint and help to prevent stretch of the fabric in the area covered thereby.

It will be noted from Figs. 6 to 8 that the thickness of the fabric in the area of the joint is not increased, and, in fact, by application of sufficient pressure, it is possible to even slightly decrease the thickness at this point if it should be desired to do so.

It will be observed by comparison of Figs. 6 and 7 that when the fabric is stretched, the rubber threads 17 and the textile threads, of which only the threads 19 are shown in these figures, are elongated and separated in the area adjacent that to which the bonding material has been applied but are unaffected in the latter area. There is practically no stretch in the bonded section, and no changes in condition of the fabric occur which would tend to loosen the rubber threads from the textile threads and cause them to recede from the point of juncture and thus weaken the joint, as has been the case with former constructions. Instead of being the weakest point in the garment, as in former constructions, the joint becomes the strongest point, and holds firmly even though the joint may be on a curve or at an angle.

When one or both of the facing strips are omitted, there may be a slight stretch in the bonding material, as evidenced by some contraction thereof near the edges of the bonded section as shown in Fig. 8, but even in this form of the joint the area near the edges of the fabric and in the link 24 between said edges, is practically non-elastic and serves to immobilize the portions of the elastic fabric where failure has usually occurred in prior constructions.

As has been previously mentioned, the principles of the invention may be applied for the purpose of immobilizing a section of an elastic fabric elsewhere than in the vicinity of a joint, and in Fig. 1 of the drawing we have shown, in opposite sides of the belt near the points where the leg bands are attached, sections 25 treated substantially as has been described with reference to the joint 16. These sections serve to prevent undue stretching of the belt in the vicinity of the points of attachment of the leg bands and tend to maintain a fixed right-angle relationship between the belt and the ends of the bands so as to prevent undue strain at the point of attachment. It will be understood that these treated sections may or may not be employed in the supporter, but from certain standpoints they are advantageous, and they are an example of the application of the principles of the invention to a section of the fabric where there is no joint.

Furthermore, the invention, as hereinbefore indicated, is applicable in forming lap joints or in joining pieces of fabric elsewhere than at the edges thereof, the form of joint illustrated being only one example of the various forms which may be made by the mechanism described.

For the sake of simplicity and because such fabrics are commonly used, we have shown in the detailed views of the drawing an elastic fabric which is stretchable in only one direction, namely that in which the threads 17 extend. However, elastic fabrics which are stretchable in two directions are also in common use, a specific example being that of the pouch material 11 shown roughly in Fig. 1, and the invention may also be utilized with such two-way stretch material, its advantages in this case being even greater than with the material specifically illustrated, since still more severe requirements are imposed on the joint when the material stretches in two directions instead of only one.

The foregoing detailed description has been given for clearness of illustration only, and no unnecessary limitations should be understood therefrom, but the appended claims should be construed as broadly as permissible in view of the prior art.

We claim:

1. A garment comprising two or more pieces of material one or more of which is an elastic fabric, and means forming a bonded joint between two pieces of said material at least one of which is elastic fabric, said means comprising a thermosetting bonding material connecting said two pieces and filling substantially all the interstices of a portion of the elastic fabric adjacent the point of connection and rendering said portion substantially non-elastic and free from internal changes such as normally occur in elastic fabric in the stretching and relaxing thereof.

2. A garment comprising two or more pieces of material one or more of which is an elastic fabric, and means forming a bonded joint between two pieces of said material at least one of which is elastic fabric, said means comprising a thermosetting bonding material connecting said two pieces and filling susbtantially all the interstices of a portion of the elastic adjacent the point of connection and rendering said portion substantially non-elastic and free from internal changes such as normally occur in elastic fabric in the stretching and relaxing thereof, and a reinforcing strip of non-elastic material adhering to said bonding material.

3. A garment including sections one or more of which is made of elastic fabric, said elastic fabric comprising non-elastic textile threads and elastic rubber threads arranged among said non-elastic threads to form, in combination with said textile threads, a highly porous, extensible structure with interstices therein, a joint between sections of said garment including a section of said elastic fabric, said joint comprising an impregnation of rubber substantially completely filling the interstices of said porous fabric in the area at the joint, thereby filling the fabric at least from the center to the outermost threads of the elastic fabric in a matrix of rubber, and a strong link of rubber integral with said matrix located between the juxtaposed portions of the garment, and a layer of strong, non-extensible fabric incorporated in the rubber matrix and link, extending from the face of one member of the garment to the opposite member, said unital link and matrix with said non-extensible fabric forming a strong, self-sufficient joint in which the extensible properties of the elastic fabric within the matrix are practically destroyed and rendered inoperative.

4. A garment including sections one or more of which is made of elastic fabric, said elastic fabric comprising non-elastic textile threads and elastic rubber threads arranged among said non-elastic threads to form, in combination with said textile threads, a highly porous, extensible structure with interstices therein, and a joint between sections of said garment including a section of said elastic fabric, said joint comprising an impregnation of rubber substantially completely filling the interstices of said porous fabric in the area at the joint, thereby filling the fabric at least from the center to the outermost threads of the elastic fabric in a matrix of rubber, and a strong link of rubber integral with said matrix located between juxtaposed portions of the garment, said unital matrix and link forming a strong, self-sufficient and substantially non-elastic joint in which the extensible properties of the elastic fabric within the matrix are practically destroyed and rendered inoperative.

5. A garment including sections one or more of which is made of elastic fabric, said elastic fabric comprising non-elastic textile threads and elastic rubber threads arranged among said non-elastic threads to form, in combination with said textile threads, a highly porous, extensible structure with interstices therein, and a joint between sections of said garment including a section of said elastic fabric, said joint comprising an impregnation of thermosetting bonding material substantially completely filling the interstices of said porous fabric in the area at the joint, thereby filling the fabric at least from the center to the outermost threads of the elastic fabric in a matrix of said bonding material, and a strong link of said bonding material integral with said matrix located between juxtaposed portions of the garment, said unital matrix and link forming a strong, self-sufficient and substantially non-elastic joint in which the extensible properties of the elastic fabric within the matrix are practically destroyed and rendered inoperative.

6. An elastic fabric having a section in which the elastic properties of the fabric have been practically nullified and the possibility of internal changes in the relationship of the threads has been practically eliminated by reason of the presence in said section of a thermosetting bonding material which fills substantially all the interstices and adheres to substantially all the threads of the fabric in said section.

7. A garment comprising two or more pieces of material one or more of which is an elastic fabric, and means forming a bonded joint between two pieces of said material at least one of which is elastic fabric, said means comprising a thermosetting bonding material connecting said two pieces and filling substantially all the interstices of a portion of the elastic adjacent the point of connection and rendering said portion substantially non-elastic and free from internal changes such as normally occur in elastic fabric in the stretching and relaxing thereof, said elastic fabric containing rubber threads and the bonding material adhering to the end portions of said threads and securely holding the same in fixed position in the fabric.

8. An elastic fabric having a section in which the elastic properties of the fabric have been practically nullified and the possibility of internal changes in the relationship of the threads has been practically eliminated by reason of the presence in said section of a bonding material comprising vulcanized rubber which fills substantially all the interstices and adheres to substantially all the threads of the fabric in said section.

9. A garment comprising two or more pieces of material one or more of which is an elastic fabric, and means forming a bonded joint between two pieces of said material at least one of which is elastic fabric, said means comprising a bonding material of vulcanized rubber connecting said two pieces and filling substantially all the interstices of a portion of the elastic fabric adjacent the point of connection and rendering said portion substantially non-elastic and free from internal changes such as normally occur in elastic fabric in the stretching and relaxing thereof.

10. A garment comprising two or more pieces of material one or more of which is an elastic fabric, and means forming a bonded joint between two pieces of said material at least one of which is elastic fabric, said means comprising a thermosetting bonding material connecting said two pieces and filling substantially all the interstices of a portion of the elastic adjacent the point of connection and rendering said portion substantially non-elastic and free from internal changes such as normally occur in elastic fabric in the stretching and relaxing thereof, said bonding material being applied on both sides of the elastic fabric and filling the interstices in said portion thereof throughout the entire thickness of the fabric to thereby immobilize the threads in said portion and thus prevent relative movement thereof.

11. A garment comprising two or more pieces of material one or more of which is an elastic fabric, means forming a bonded joint between two pieces of said material at least one of which is elastic fabric, said means comprising a thermosetting bonding material connecting said two pieces and filling substantially all the interstices of a portion of the elastic adjacent the point of connection and rendering said portion substantially non-elastic and free from internal changes such as normally occur in elastic fabric in the stretching and relaxing thereof, said bonding material being applied on both sides of the elastic fabric and filling the interstices in said portion thereof throughout the entire thickness of the fabric to thereby immobilize the threads in said portion and thus prevent relative movement thereof, and reinforcing strips of non-elastic material bonded to said bonding material on both sides of the fabric.

12. A garment including sections of fabric one or more of which is elastic fabric, said elastic fabric comprising non-elastic textile threads and elastic threads arranged among said non-elastic threads to form, in combination with said textile threads, an extensible structure, a butt joint between sections of said garment comprising a body of material thermo-adhesively bonded to and joining said sections edge to edge and pressed into the interstices of said fabric at the joint forming a matrix and rendering a portion of the elastic fabric adjacent and along said joint substantially non-elastic and free from internal changes such as normally occur in elastic fabric in the stretching and relaxing thereof.

13. A garment including sections of fabric one or more of which is elastic fabric, said elastic fabric comprising non-elastic textile threads and elastic threads arranged among said non-elastic threads to form, in combination with said textile threads, an extensible structure, a joint between sections of said garment comprising a body of material thermo-adhesively bonded to and joining said sections and pressed into the interstices of said fabric at the joint forming a matrix and rendering a portion of the elastic fabric adjacent and along said joint substantially non-elastic and free from internal changes such as normally occur in elastic fabric in the stretching and relaxing thereof.

14. A garment including sections of fabric one or more of which is elastic fabric, said elastic fabric comprising non-elastic textile threads and elastic threads arranged among said non-elastic threads to form, in combination with said textile threads, an extensible structure, a joint between sections of said garment comprising a body of material thermo-adhesively bonded to and joining said sections and pressed into the interstices of said fabric at the joint forming a matrix and rendering a portion of the elastic fabric adjacent and along said joint substantially non-elastic and free from internal changes such as normally occur in elastic fabric in the stretching and relaxing thereof, and a reinforcing strip of non-elastic material similarly bonded to said joint.

15. An athletic supporter including belt, pouch and leg-band sections of fabric the belt section of which is elastic fabric comprising non-elastic textile threads and elastic threads arranged among said non-elastic threads to form, in combination with said textile threads, an extensible structure, a joint between sections of said garment comprising a body of material thermo-adhesively bonded to and joining said belt section and the top portion of said pouch section and pressed into the joint forming a matrix and rendering a portion of the elastic fabric adjacent and along said joint substantially non-elastic and free from internal changes such as normally occur in elastic fabric in the stretching and relaxing thereof, said leg-band sections connecting the bottom of the pouch section and respective side portions of said belt section.

16. An athletic supporter including belt, pouch and leg-band sections of fabric the belt section of which is elastic fabric comprising non-elastic textile threads and elastic threads arranged among said non-elastic threads to form, in combination with said textile threads, an extensible structure, a joint between sections of said garment comprising a body of material thermo-adhesively bonded to and joining said belt section and the top portion of said pouch section and pressed into the joint forming a matrix and rendering a portion of the elastic fabric adjacent and along said joint substantially non-elastic and free from internal changes such as normally occur in elastic fabric in the stretching and relaxing thereof, a reinforcing strip of non-elastic material similarly bonded to said joint and extending across at least one face of said joint and overlapping said belt and pouch sections, and said leg-band sections connecting the bottom of the pouch section and respective side portions of said belt section.

17. An athletic supporter including belt, pouch and leg-band sections of fabric at least the belt section of which is elastic fabric comprising non-elastic textile threads and elastic threads arranged among said non-elastic threads to form, in combination with said textile threads, an extensible structure, a butt joint of inverted V-shape between sections of said garment comprising a body of material thermo-adhesively bonded to and joining the ends of said belt section and the top portion of said pouch section edge to edge and pressed into the joint forming a matrix and rendering a portion of the elastic fabric adjacent and along said joint substantially non-elastic and free from internal changes such as normally occur in elastic fabric in the stretching and relaxing thereof, said leg-band sections connecting the bottom of the pouch section and respective side portions of said belt section.

18. An elastic fabric as claimed in claim 6, wherein the said section is nevertheless flexible and moulded to a desired shape.

19. An elastic fabric as claimed in claim 6, wherein the said section includes a reinforcing strip of non-elastic material adhering to said bonding material.

DANA E. MORRISON.
PAUL F. ZIEGLER.

REFERENCES CITED

The following references are of record in the file of this patent:

UNITED STATES PATENTS

| Number | Name | Date |
|---|---|---|
| 1,063,062 | Quenzer | May 27, 1913 |
| 1,715,702 | Gordon | June 4, 1929 |
| 1,896,646 | Philips | Feb. 7, 1933 |
| 1,914,148 | Meagher | June 13, 1933 |
| 1,080,284 | Kops | Dec. 2, 1913 |